United States Patent [19]

Jevne et al.

[11] Patent Number: 4,593,053

[45] Date of Patent: Jun. 3, 1986

[54] HYDROPHILIC PRESSURE SENSITIVE BIOMEDICAL ADHESIVE COMPOSITION

[75] Inventors: Allan H. Jevne, Anoka; Brett R. Vegoe, Brooklyn Park; Carolann M. Holmblad, Cambridge; Patrick T. Cahalan, Champlin, all of Minn.

[73] Assignee: Medtronic, Inc., Minneapolis, Minn.

[21] Appl. No.: 679,653

[22] Filed: Dec. 7, 1984

[51] Int. Cl.$^4$ .................. A61K 9/70; A61K 31/79
[52] U.S. Cl. .................... 523/111; 523/105; 524/503; 424/80; 514/944
[58] Field of Search ............... 523/111, 105; 524/503; 424/80; 514/944

[56] References Cited

U.S. PATENT DOCUMENTS

| | | | |
|---|---|---|---|
| 3,892,905 | 7/1975 | Albert | 524/503 |
| 4,251,400 | 2/1981 | Columbus | 524/503 |
| 4,280,942 | 7/1981 | Green | 524/503 |
| 4,289,749 | 9/1981 | Keith et al. | 424/28 |
| 4,292,302 | 9/1981 | Keith et al. | 424/28 |
| 4,292,303 | 9/1981 | Keith et al. | 424/28 |
| 4,294,820 | 10/1981 | Keith et al. | 424/28 |
| 4,336,145 | 6/1982 | Briscoe | 524/55 |
| 4,460,562 | 7/1984 | Keith et al. | 424/28 |
| 4,492,685 | 1/1985 | Keith et al. | 424/80 |

*Primary Examiner*—Ronald W. Griffin
*Attorney, Agent, or Firm*—Grady J. Frenchick; Joseph F. Breimayer; John L. Rooney

[57] ABSTRACT

Novel, hydrophilic, skin-compatible, pressure sensitive, solid, adhesive gel hydrogel composition comprising 25 to 50 weight percent polyvinyl pyrolidone (PVP) preferably having a molecular weight in the range of about 100,000 to 600,000, 2 to 5 weight percent polyvinyl alcohol (PVA) preferably having a molecular weight in the range of about 150,000 to 300,000, about 5 to about 40 weight percent humectant, about 3 to about 50 weight percent water, about 0 to about 50 weight percent of an ionic species. In a preferred aspect, the composition of the invention is utilized in an iontophoresis device to provide a hydrophilic gel matrix from which a drug is iontophoretically delivered.

11 Claims, No Drawings

HYDROPHILIC PRESSURE SENSITIVE BIOMEDICAL ADHESIVE COMPOSITION

DESCRIPTION OF THE INVENTION

This invention relates to a novel, hydrophilic, skin-compatible, pressure sensitive, adhesive gel composition. The composition of the present invention is referred to as a "gel" or "hydrogel" and is known to be particularly advantageous in biomedical applications such as sensing or stimulating electrodes, in electrosurgery (e.g., an electrocautery ground electrode), wound management or drug delivery. In a preferred practice of the invention, the present adhesive gel is employed in active or passive transdermal drug delivery. In yet another preferred practice of the present invention, an ionic species including ionic drugs or salts are added to the present composition to increase its conductivity.

BACKGROUND OF THE INVENTION

U.S. Pat. Nos. 4,292,302, 4,292,303, 4,289,749 and 4,294,820 describe a polymeric diffusion matrix in which there is dispersed terbutaline, clonidine, phenylpropanolamine and phenylephrine, respectively. These four patents in the name of Alec D. Keith et al and commonly assigned to Key Pharmaceuticals, Inc. differ only in having different drugs, the incorporation of which is described in each patent. As will be more completely described below, the polymeric drug diffusion matrix of the Keith et al patents suffers the drawback of being unstable with respect to the water and humectant included therein. Put otherwise, the drug diffusion matrix of the Keith et al patents tends to synerese, i.e. to exude the liquid, water component of the gel.

U.S. Pat. No. 4,460,562 also to Keith, et al titled "Polymeric Diffusion Matrix Containing Propranolol" describes diffusion matrix comprising from about 1 to about 60% of a polar plasticizer (e.g., glycerol), from about 6 to about 30% by weight of at least 90% hydrolyzed polyvinyl alcohol having a molecular weight of about 50,000 to about 150,000, from about 2 to about 30% by weight polyvinyl-pyrrolidone having a molecular weight of about 15,000 to about 85,000 and a pharmaceutically transdermally effective amount of propranolol. As is more completely discussed in the examples this material has inferior adhesion to skin, does not have good elongation and also tends to synerese. Furthermore, the materials of the Keith et al patents are not pressure sensitive adhesives.

The present invention tends to overcome the problems exhibited by the prior art (Keith et al) polymeric diffusion matrices to provide an advantageously skin-compatible, solid, gel (or hydrogel), biomedical adhesive composition.

SUMMARY OF THE INVENTION

Briefly, in one aspect, the present invention is a novel, hydrophilic, pressure sensitive, biomedical adhesive composition comprising about 25 to 50 weight percent (preferably about 30 to 40 weight percent) polyvinyl pyrrolidone (PVP), about 2 to about 5 weight percent (preferably about 3 to 4 weight percent) polyvinyl alcohol (PVA), about 5 to 40 weight percent polar plasticizer or humectant, about 3 to 50 weight percent water and, depending upon the application, a pharmaceutically effective amount of a desired drug or sufficient ionic species to provide conductivity to the composition. Generally speaking, the amount of an ionic species or a drug (which may be also be ionic) would be from about 0 to 50 weight percent of the composition.

DETAILED DESCRIPTION OF THE INVENTION

As noted above, the present novel, biomedical adhesive gel composition exhibits the critically important property of not syneresing (i.e., exuding water or humectant). The composition of the first four of the Keith et al patents metioned above is generally in the range of 2 to 10 weight percent polyvinyl pyrrolidone, 6 to 20 weight percent polyvinyl alcohol, 2 to 60 weight percent polar plasticizer (e.g., glycerol or polyethylene glycol) and a pharmaceutically effective amount of a drug. While no particular range of water is disclosed or claimed in any of the Keith et al patents, the examples in, e.g., the '820 patent, indicate weight percentages of water of 45, 70, and 66. Thus, consistent with the above description of the present invention, the critical advantage achieved herein by virtue of having a higher molecular weight and different amounts of PVA and PVP is a stable, non-syneresing, adhesive composition. For a preferred iontophoretic use of the present composition the low concentration of ionic impurities provides more efficient iontophoretic drug delivery. The critical advantages achieved by the present composition are more fully described in the examples which follow.

The present invention contemplates the utilization of from 25 to 50 weight percent polyvinyl pyrrolidone (PVP) with a preferred range of 30 to 40 weight percent. The polyvinyl pyrrolidone employed in the present invention has a weight average molecular weight in the range of about 100,000 to 600,000, preferably falling in the range of about 300,000 to 400,000. A particularly suitable polyvinyl pyrrolidone as employed in the present invention is type NP-K90 commercially available from the GAF Corp. Chemical Products.

The present invention also contemplates the presence of polyvinyl alcohol in a weight percentage of about 2 to 5 preferably about 3 to 4 weight percent. A particularly advantageous polyvinyl alcohol such as can be employed in the present invention is sold by the E. I. DuPont de Nemours & Co. under the trade designation "Elvanol HV". Generally speaking, polyvinyl alcohol suitably employed in the present invention would have a weight average molecular weight in the range of 150,000 to 300,000, preferably about 170,000 to 220,000. A particularly preferred PVA is the material available from E. I. du Pont de Nemours & Co. having a stated molecular weight of about 185,000.

The polyvinyl alcohols of this invention are generally at least about 75% hydrolyzed. Preferably, useful PVA is about 100% hydrolyzed. Percentage of hydrolysis is not thought to be critical in this invention.

The present invention also contemplates the presence of from about 5 to 40 weight percent, preferably about 15 to 25 weight percent polar plasticizer or humectant e.g., glycerol. Other useful polar plasticizers include propylene glycol, sorbitol, poly(ethylene)glycol preferably having a molecular weight in the range of about 200 to 20,000, or polypropylene glycol preferably having a molecular weight in the range of about 500 to 5,000. Other polar plasticizers or humectants will be well-known to one skilled in the hydrogel art.

The present biomedical adhesive composition also contemplates the presence of about 3 to 50 weight percent water in the resulting matrix. Deionized water is preferred. This percentage of water, which is advantageously maintained in the present composition, provides suitable adhesiveness, tack, cohesive strength, and skin-compatibility.

Lastly, the present adhesive composition optionally contemplates the presence of an ionic species or a drug (which may also be ionic). The selection of an ionic species or a particular drug will be dependent upon the intended utilization of the completed composition. If the present adhesive composition is to be used to hold an iontophoresis electrode in contact with a patient's skin and to provide a reservoir for the drug, then the drug which is to be iontophoretically delivered would be mixed in the present matrix. If the present composition is to be employed to maintain an electrocardiogram electrode in place and to provide a quality sensing capability, then a suitable ionic species e.g., KCl would be employed in the composition to provide the desired conductivity. While both drug or a conductive salt are optionally included in the present composition, the present composition may be employed in other applications, (e.g., wound dressings) which do not require a conductive material, in which case neither a drug nor an ionic species would be present.

One skilled in the present art will recognize that it is possible to add small amounts of other materials to adjust the properties of the present composition for a particular end use. For example, if it is desirable to increase the tackiness of the gel, poly-2-acrylamido 2-methyl propane sulfonic acid poly (AMPS) (or its salts) may be employed. Other material which can be employed to increase tackiness include polyacrylic acid, polystyrene sulfonic acid or salts thereof, karaya, xanthan, guar or locust bean gums. Tackifiers above described would generally be present in the range of about 2 to 20 weight percent.

For some applications, it may be desirable to increase the internal coherence, cohesiveness or strength of the present biomedical composition. In such instances, materials such as hydroxy propyl methyl cellulose, carboxy methyl cellulose, hydroxy propyl guar, dextran or silica may be added. One skilled in the present art will recognize other materials which could be added to the composition described herein to adjust various desired properties. Generally speaking, such additives would be present in the range of about 0 to 10 weight percent.

Preparation of the materials of the present invention is relatively straightforward. Generally speaking, a temperature-controlled, stirrable reactor is employed. Thus a reactor would be preheated to about 90° C., set to mix at approximately 100 revolutions per minute, and the following materials (in representative quantities):

1. deionized H<sub>2</sub>O—39 weight percent
2. glycerol polar plactizers (Mallinckrodt, Inc.)—22 weight percent
3. polyvinyl alcohol (duPont Elvanol HV)—4 weight percent
4. polyvinyl pyrrolidone (GAF Company 360,000 molecular weight)—35 weight percent would be mixed, preferably in the order indicated. The temperature of the closed mixer then would be increased to approximately 130° C. while maintaining stirring. After a temperature of approximately 130° C. is obtained, the temperature of the mixture would be decreased to approximately 95° C., the mixer subsequently turned off and the material poured onto a release paper (e.g., "Polyslick"), the gel thereby being cooled to a solid, non-liquid state.

EXAMPLES 1–8

Using the general procedures set out above, 8 gels were prepared. These materials were then evaluated for their adhesion to skin, adhesion to 304 stainless steel, ultimate tensile strength, 100% secant modulus and percent elongation. The tendency to synerese of these materials also was subjectively evaluated. The compositions of the respective examples and the evaluations are set out in Table I:

TABLE I

| Composition (% w/w) | Example Number | | | |
|---|---|---|---|---|
| | 1 | 2 | 3 | 4 |
| 360,000 MW PVP | 32 | 31 | 36 | 29 |
| Elvanol HV PVA | 4 | 4 | 3.5 | 4 |
| 40,000 MW PVP | — | — | — | — |
| 115,000 MW PVA | — | — | — | — |
| Glycerol | 24 | 22 | — | 24 |
| Sorbitol | — | — | 5 | — |
| PEG 600 | — | — | 15 | — |
| D.I. H<sub>2</sub>O | 35 | 35 | 34 | 27 |
| KCl | 5 | — | — | — |
| Na Acetate | — | 8 | 6.5 | — |
| Na Salicylate | — | — | — | 16 |
| % skin adhesion | 20 | 20 | 35 | 70 |
| Adhesion to 304 S.S. | 136 g/in. | 45 g/in. | 91 g/in. | 45 g/in. |
| Ultimate tensile st. (psi) | 10 | 15 | 35 | 15 |
| 100% Secant modulus (psi) | 3 | 8 | 10 | 4 |
| % Elongation | 700 | 700 | 800 | 900 |
| Syneresis* | No | No | No | No |
| | 5 | 6 | 7 | 8 |
| 360,000 MW PVP | 40 | — | — | — |
| Elvanol HV PVA | 4 | — | — | 4 |
| 40,000 MW PVP | — | 30 | 8 | 32 |
| 115,000 MW PVA | — | 6 | 15 | — |
| Glycerol | — | 20 | 30 | 24 |
| Sorbitol | — | — | — | — |
| PEG 600 | 16 | — | — | — |
| D.I. H<sub>2</sub>O | 40 | 39 | 47 | 35 |
| KCl | — | 5 | — | 5 |
| Na Acetate | — | — | — | — |
| Na Salicylate | — | — | — | — |
| % skin adhesion | 60 | 0 | 0 | 0 |
| Adhesion to 304 S.S. | 136 g/in. | <5 g/in. | 0 g/in. | <5 g/in. |
| Ultimate tensil st. (psi) | 17 | 14 | 125 | 4 |
| 100% Secant modulus (psi) | 5 | 5 | 51 | 1 |
| % Elongation | 650 | 240 | 190 | 170 |
| Syneresis* | No | Yes | Yes | Yes |

*to the point of exuding liquid.

Several observations may be made about the data contained in Table I. First of all, the test procedures employed for the various measurements taken were as follows:

Skin adhesion: The percentage indicated is the approximate area of a patch of test material remaining in intimate human skin contact after a 6 hour wearing period. A zero reading means that the test patch of material did not adhere to skin through the entire 6 hour period of the test.

Adhesion to 304 stainless steel: The numbers indicated are the force needed to peel a 1"×5" strip of the test material from the indicated substrate. Samples were smoothed onto the stainless steel substrate by hand and all air bubbles squeezed out. The samples then were permitted to rest for 24 hours before the test was run. The numbers are averages of the force needed to peel the sample from the substrate using an Instron tensile tester at a cross head speed of 5 inches per minute.

Ultimate tensile test: Using an "Instron" tensile tester, the tensile strength of the various samples was determined using a cross speed of 5 inches per minute, 10 pounds full scale load. 1"×2" rectangular samples were employed, ultimate tensile strength being the maximum force applied (to breaking) divided by the cross-sectional area of the sample.

100% secant modulus: 100% secant modulus was determined by dividing the force applied when the sample had been stretched 1 inch (in the above tensile test) by the cross-sectional area of the sample.

Percent elongation at break: This is calculated by dividing the distance the cross-head (e.g., of an "Instron" tensile tester) had traveled to sample break by the original length of the sample and multiplying the result by 100.

The first 5 examples in Table I are materials of the present invention. The material of Example 6 is one prepared substantially in accordance with Keith et al U.S. Pat. No. 4,460,562. Example 7 was prepared in accordance with Keith et al U.S. Pat. No. 4,393,302. Example 8 is prepared substantially the same as the material of Example 1 (i.e., a material of this invention) with the exception that the preferred lower molecular weight PVP of the Keith et al patent was employed. An examination of the results indicates that all three of the Keith et al materials tended to synerese. Further, the three materials did not provide identifiable adhesion to skin and exhibited poor adhesion to stainless steel. Percent elongation at break was also very low. Tensile strength and secant modulus were greater for the Keith et al materials than for the materials of the present invention. This was due to the fact that the material of this invention is conformable and elastomeric. These data illustrate the importance of the molecular weight and composition percentage differences of the material of this invention versus that of the Keith et al patents.

EXAMPLES 9–12

Using the general synthetic process described above, a number of gels were prepared utilizing different additives to enhance tackiness of the resulting gel. The composition of these materials are set out in Table II. In each of each of examples 9–12, the polyvinyl pyrrolidone was the 360,000 molecular weight material commercially available from GAF. The polyvinyl alcohol was "Elvanol HV" available from E. I. duPont de Nemours & Co. In examples 9 and 10, the additive was poly(2-acrylamido 2-methyl propane sulfonic acid) commercially available from Henkel Corporation under the trade designation "Rheothik 80-L". In example 11, the additive was karaya and in 12 polyacrylic acid "Goodright K732" commercially available from Goodyear Chemicals. Generally the tackifier additive replaces a portion of the PVP.

EXAMPLES 13–15

A number of compositions of the invention were prepared in accordance with the above procedure in which additives were included to increase the cohesive strength of the gel. In example 13, 3.0 percent hydroxy propyl guar was employed. In example 14, 5.1 percent of silica ("M-5 Cabosil") commercially available from Cabot Corporation was employed. In example 15, 3% hydroxypropyl methyl cellulose was employed. Overall composition of the respective materials of examples 13–15 are shown in Table III.

TABLE II

| Example No. | % PVP | % PVA | % Glycerol | % Water | Tack Enhancer W/W |
|---|---|---|---|---|---|
| 9 | 28.9 | 3.5 | 36.2 | 26.7 | 4.7 |
| 10 | 16.8 | 4.9 | 37.8 | 34.3 | 6.2 |
| 11 | 18.0 | 4.0 | 41.0 | 22.0 | 15.0 |
| 12 | 13.8 | 5.0 | 37.2 | 22.0 | 22.0 |

TABLE III

| Example No. | % PVP | % PVA | % Glycerol | % Water | Strength Enhancers W/W |
|---|---|---|---|---|---|
| 13 | 31 | 4.0 | 22.0 | 40 | HPG 3% Hydroxypropyl guar |
| 14 | 29 | 4.0 | 25.0 | 37 | M-5 silica 5% |
| 15 | 31 | 4.0 | 22.0 | 40 | HPMC 3% |

EXAMPLES 16–19

A number of different compositions contemplated by the present invention were synthesized using the procedure above in which various polor plasticizers were substituted for the plasticizer glycerol. In example 16, sorbitol, commercially available from Aldrich Chemical, was employed. In examples 17 and 18, poly(ethylene glycol) molecular weight 600 was employed. In example 19, poly(propylene glycol) molecular weight 725 was employed. The overall compositions of the materials of examples 16–19 are set forth in Table IV.

TABLE IV

| Example No. | % PVP | % PVA | % Water | Polar Plasticizer % |
|---|---|---|---|---|
| 16 | 33.0 | 4.0 | 28.0 | 41.0 |
| 17 | 40.0 | 4.0 | 40.0 | 41.0 |
| 18 | 28.6 | 4.0 | 35.0 | 37.1 |
| 19 | 33.0 | 4.0 | 30.0 | 41.0 |

EXAMPLE 20

An electrocardiogram (ECG) electrode gel was prepared utilizing polyvinyl pyrrolidone, PVA, glycerol, the ionized water and potassium chloride. The material was tested on an ECG electrode and showed acceptable electrical characteristics with respect to impedance, offset voltage, instability, defibrillation offset, defibrillation recovery and 10 Hz alternating current impedance.

EXAMPLE 21

Composition of the present invention was synthesized according to the above procedure and employed as a stimulating gel with a transcutaneous electronic nerve stimulator unit. Acceptable electrical stimulation was found particularly when silica (Cab-O-Sil M-5) was employed in the 4–6 percent range.

EXAMPLE 23

A composition of the present invention was employed in conjunction with pilocarpine nitrate (Sigma Chemical Corporation) to demonstrate the effectiveness of the present composition as an iontophoresis gel. Pilocarpine nitrate was iontophoretically driven into a subject's skin thus inducing delivery of sweat and demonstrating the utility of the present composition as an iontophoresis electrode adhesive/drug reservoir material.

EXAMPLE 23

To a breaker at room temperature 30 g glycerol and 45 ml water were added and mixed. The beaker and mixture was heated. When 70° C. was reached, 15 g of 100% hydrolyzed 115,000 molecular weight polyvinyl alcohol and 8 g 40,000 molecular weight polyvinyl pyrrolidone were added. Heating and stirring were continued until the mixture reached the temperature of 90° C. and all ingredients were in solution. The mixture then was poured onto a release paper to a thickness of 2 to 3 mm and permitted to cool until gelation occurred.

The synerese characteristics of the material prepared above (0.125 in. thick) then was monitored. Approximately 59.8 g of the gelled material was placed between two sheets of Polyslick release liner and sealed into a polyethylene bag. Over time, the weight of the gelled material in the bag was as follows:

24 hrs: 54.5 g*
28 hrs: 51.5 g*
72 hrs: 48.9 g*
96 hrs: 46.6 g*
1 week: 44.5 g*
2 weeks: 40.8 g*

*liquid in the bag

Utilizing the test procedures described above, the ultimate tensile strength was measured to be 125 psi, the 100% modulus was 51 psi and the percent elongation was determined to be 190%. From this data and observations, it is seen the material of the Keith et al patents does not exhibit the stability and desirable performance characteristics of the material of this invention.

The above description and examples are intended to be illustrative and not limiting of the present invention. One skilled in the hydrogel art will appreciate that there may be many variations and alternatives suggested by the above invention. These variations and alternatives are intended to be within the scope of this invention as set forth in the following claims.

What is claimed is:

1. A skin-compatible, hydrophilic adhesive composition comprising:
   25 to 50 weight percent polyvinyl pyrrolidone having a molecular weight in the range of 100,000 to 600,000;
   2 to 5 weight percent polyvinyl alcohol having a molecular weight in the range of 150,000 to 300,000;
   5 to 40 weight percent polar plasticizer;
   3 to 50 weight percent water; and
   about 0 to 50 weight percent of an ionic or nonionic species.

2. A biomedical adhesive according to claim 1 wherein there is from about 30 to 40 weight percent polyvinyl pyrrolidone.

3. A biomedical composition according to claim 1 wherein there is about 3 to 4 weight percent polyvinyl alcohol.

4. A biomedical composition according to claim 1 wherein the polyvinyl pyrrolidone has a molecular weight in the range of about 300,000 to 400,000.

5. A biomedical composition according to claim 1 wherein the polyvinyl alcohol has a molecular weight in the range of about 170,000 to 220,000.

6. A biomedical composition according to claim 1 wherein the polar plasticizer is glycerol.

7. A biomedical composition according to claim 1 wherein the polar plasticizer is sorbitol.

8. A biomedical composition according to claim 1 wherein the polar plasticizer is poly(ethylene)glycol.

9. A biomedical composition according to claim 1 which further includes from about 0 to about 20 weight percent of an additive.

10. A biomedical composition according to claim 9 wherein the additive is selected from the group consisting of hydroxy propyl methyl cellulose, carboxy methyl cellulose, cellulose, hydroxy propyl guar, dextran or silica.

11. A composition according to claim 1 which includes an additive selected from the group consisting of poly-2-acrylamido 2-methyl propane sulfonic acid, polyacrylic acid, polystyrene sulfonic acid, salts thereof, karaya, xanthan, guar or locust bean gums.

* * * * *